United States Patent [19]

Mackrodt et al.

[11] 4,362,573
[45] Dec. 7, 1982

[54] STABILIZED CHLORINATED SOLVENTS

[75] Inventors: William C. Mackrodt, Hale; Richard B. Jones, Weaverham; Neil Winterton, Chester, all of England

[73] Assignee: Imperial Chemical Industries Limited, London, England

[21] Appl. No.: 172,974

[22] Filed: Jul. 28, 1980

[30] Foreign Application Priority Data

Aug. 7, 1979 [GB] United Kingdom ............... 7927414

[51] Int. Cl.$^3$ .................. B08B 5/00; C07C 17/42; C23G 5/02
[52] U.S. Cl. ........................ 134/31; 134/40; 106/311; 252/171; 252/172; 252/407; 252/364; 570/114; 570/116
[58] Field of Search ............... 106/311; 260/652.5 R; 252/171, 172, 153, 162, 407, 364; 134/40, 31; 570/114, 116

[56] References Cited

U.S. PATENT DOCUMENTS

| | | | |
|---|---|---|---|
| 2,671,064 | 3/1954 | Cowell et al. | 260/652.5 R |
| 3,260,760 | 7/1966 | Domen et al. | 260/652.5 R |
| 3,397,246 | 8/1968 | Ryekaert et al. | 260/652.5 R |
| 3,629,128 | 12/1971 | Rains | 106/311 |
| 3,663,255 | 5/1972 | Vivian | 106/311 |
| 3,723,332 | 3/1973 | Barton | 260/652.5 R |
| 4,189,397 | 2/1980 | Allen | 570/114 |
| 4,287,003 | 9/1981 | Allen | 570/116 |

FOREIGN PATENT DOCUMENTS

| | | | |
|---|---|---|---|
| 48-681 | 1/1973 | Japan | 260/652.5 R |
| 49-14406 | 2/1974 | Japan | 260/652.5 R |
| 49-134604 | 12/1974 | Japan . | |
| 50-121203 | 9/1975 | Japan | 260/652.5 R |
| 50-121204 | 9/1975 | Japan | 260/652.5 R |
| 50-28928 | 9/1975 | Japan | 260/652.5 R |
| 50-14605 | 12/1975 | Japan . | |

*Primary Examiner*—Allan Lieberman
*Attorney, Agent, or Firm*—Cushman, Darby & Cushman

[57] ABSTRACT

A solvent composition comprising 1,1,1-trichloroethane and a stabilizing amount of an epoxide of formula

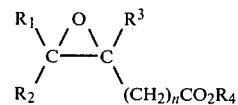

wherein
$R_1$ and $R_2$ are hydrogen, alkyl of 1 to 4 carbon atoms, phenyl or benzyl,
$R_3$ is hydrogen or alkyl of 1 to 4 carbon atoms,
$R_4$ is alkyl of 1 to 4 carbon atoms
and n is 0 or 1.

Preferably the or each alkyl group contains 1 or 2 carbon atoms; examples of useful epoxides are ethyl trans-2,3-epoxybutyrate, ethyl 3,4-epoxy-3-methylvalerate and ethyl beta-methyl-beta-phenylglycidate.

12 Claims, 1 Drawing Figure

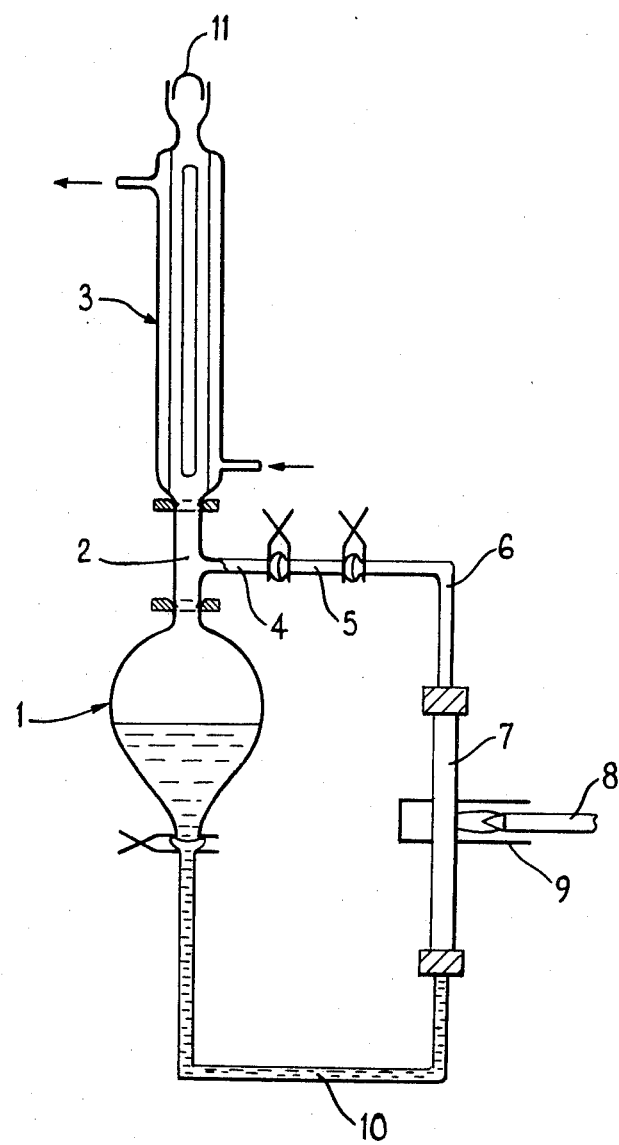

STABILIZED CHLORINATED SOLVENTS

This invention relates to the stabilisation of chlorinated aliphatic hydrocarbons.

In recent years there has been rapidly expanding use of chlorinated aliphatic hydrocarbons, especially 1,1,1-trichloroethane, in industrial cleaning processes, particularly in the degreasing of metals. However large scale use of 1,1,1-trichloroethane presents difficulties since in contact with iron, zinc, aluminium and copper there is attack on the solvent. This leads to tar formation and evolution of large amounts of acid.

We have now found that compounds, not hitherto proposed, which are specific epoxy compounds are effective in the stabilisation of 1,1,1-trichloroethane.

According to the present invention there is provided a solvent composition comprising 1,1,1-trichloroethane and a stabilising amount of an epoxide of formula

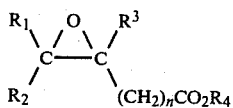

wherein $R_1$, $R_2$ and $R_3$ (which may be the same or different) represent hydrogen atoms or alkyl groups having 1 to 4 carbon atoms and wherein $R_1$ or $R_2$ may also be a phenyl group or a benzyl group, n is 0 or 1 and $R_4$ is an alkyl group having 1 to 4 carbon atoms.

Preferably the alkyl groups represented by $R_1$, $R_2$, $R_3$ and $R_4$ contain 1 or 2 carbon atoms.

In one form of the invention $R_1$ and $R_4$ are alkyl groups and $R_2$ and $R_3$ are hydrogen atoms. One such useful compound is provided when $R_1$ is a methyl group, $R_4$ is an ethyl group, $R_2$ and $R_3$ are hydrogen and n is 0, that is, the compound ethyl trans-2,3-epoxybutyrate. A mixture of the cis and trans isomers can be employed, if desired.

In another form of the invention $R_1$, $R_3$ and $R_4$ are alkyl groups and $R_2$ is hydrogen. One such useful compound is provided wherein $R_1$ and $R_3$ are methyl groups, $R_2$ is hydrogen, $R_4$ is an ethyl group and n is 1, that is, the compound ethyl 3,4-epoxy-3-methylvalerate. The latter compound may be a mixture of the cis- and trans- isomers.

In yet another form of the invention $R_1$ and $R_4$ are alkyl groups, $R_2$ is a phenyl group, and $R_3$ is hydrogen. One such useful compound is provided wherein $R_1$ is a methyl group, and $R_4$ is an ethyl group, $R_2$ is a phenyl group, $R_3$ is hydrogen and n is 0, that is, the compound ethyl beta-methyl-beta-phenylglycidate.

Mixtures of two or more of the epoxides may be used if desired.

Quite small proportions by weight of the organic epoxides, for example, 0.05% by weight or less with reference to the solvent have a stabilising effect on the solvent. Usually the proportion of the organic epoxide is not greater than 5% by weight with reference to the solvent, although larger proportions may be used, if desired.

Other known stabilisers for the solvent may also be associated with the epoxide stabilisers mentioned above. Each of these known stabilisers, when used, is usually present in an amount of not greater than 3% by weight of the solvent. Indeed considerably smaller amounts than 3% of said conventional stabilisers may be used if desired.

The present invention includes within its scope a method of inhibiting decomposition of 1,1,1-trichloroethane due to presence of metals which comprises incorporating in the solvent an organic epoxide as specified above.

The invention also includes within its scope a method of degreasing metal or other articles which comprises bringing them into contact with 1,1,1-trichloroethane stabilised with said organic epoxides, or the vapour thereof which solvent may, if desired, also contain conventional stabilisers.

The following Examples illustrate the invention. Where percentages are mentioned they are by weight, with reference to the solvent.

EXAMPLE 1

The apparatus, shown in the accompanying schematic drawing, comprised a pear-shaped glass flask (1) (100 ccs capacity) surmounted by a vertical glass tube (2) leading to a water-cooled reflux condenser (3). The tube (2) was also provided with a horizontal glass side tube (4) which abutted a second horizontal glass tube (5). The ends of both horizontal tubes were so deformed that by application of a spring clip liquid and vaporised solvent could be withdrawn from the second glass tube (5). The latter (5) abutted a third glass tube (6) which was bent at right angles to connect with a mild steel tube (7) (15 cms length, 0.64 cms diameter). Heat from a Meker burner (8) was applied through a shroud tube (9) to the middle (3 cms length) of the vertical mild steel tube (7). A glass tube (10) connected the steel tube and was bent through two right angles to connect with the bottom of the glass flask (1).

50 ccs of a stabilised 1,1,1-trichloroethane were placed in the glass flask and the solvent composition was heated to boiling. By heating the mild steel tube, stabilised 1,1,1-trichloroethane in the vapour and liquid phase passed from the mild steel tube to the glass side arms, thus acting as a thermosyphon. The circulating 1,1,1-trichloroethane was thus subjected to an accelerated stability test in the presence of mild steel. The stabilised composition was subjected to this test for a period of 120 minutes. The time taken to develop acidity in the vapour and liquid phases was determined. The vapour was that near the top of the condenser and the liquid was taken from the abutting end of the first and second glass tubes. The acidity was measured by universal litmus paper to pH3 (11) (unless otherwise stated). The results were as shown in Table I.

The stabiliser used was ethyl beta-methyl-beta-phenylglycidate, referred to hereinafter as EMPG.

Tests were carried out with 1,1,1-trichloroethane stabilised with:

(ii) EMPG together with nitromethane and dioxan
(iii) EMPG together with isopropyl nitrate, acetonitrile and nitromethane.

The results were as shown in Table I.

By way of comparison tests were carried out, not according to the invention, with 1,1,1-trichloroethane stabilised with:

(iv) 1,2-butylene oxide
(v) nitromethane and dioxan
(vi) isopropyl nitrate, acetonitrile, nitromethane
(vii) isopropyl nitrate, acetonitrile, nitromethane, 1,2-butylene oxide.

The results are given in the Comparative Table.

TABLE I

| | Stabiliser % | Time (mins) for vapour to become acidic | Time (mins) for liquid to become acidic |
|---|---|---|---|
| (i) | EMPG (0.5%) | >120 | >120 |
| (ii) | EMPG (0.5%) Nitromethane (0.5%) Dioxan (3.5%) | >120 | >120 |
| (iii) | EMPG (0.5%) Isopropyl nitrate (2%) Acetonitrile (2%) Nitromethane (0.7%) | >120 | >120 |
| COMPARATIVE TABLE | | | |
| (iv) | 1,2-butylene oxide (0.5%) | 40 | 5 |
| (v) | Nitromethane (0.5%) Dioxane (3.5%) | 6 (pH4) | 15 (pH4) |
| (vi) | Isopropylnitrate (2%) Acetonitrile (2%) Nitromethane (0.7%) | 4 | 4 |
| (vii) | Isopropylnitrate (2%) Acetonitrile (2%) Nitromethane (0.7%) 1,2-butylene oxide (0.5%) | 3 | 3 |

EXAMPLE 2

The stabiliser described in Example 1 (EMPG) was replaced by ethyl trans-2,3-epoxybutyrate, referred to hereinafter as EEB.

Tests were carried out as described in Example 1 wherein 1,1,1-trichloroethane was stabilised (a) with EEB (0.5%) together with nitromethane (0.5%) and tertiary butanol (2%) and (b) with EEB (0.5%) together with nitromethane (0.7%) isopropyl nitrate (2%) and acetonitrile (2%). The times taken before acidity developed in the vapour phase at pH3 was >120 minutes and >120 minutes, respectively.

EXAMPLE 3

The stabiliser used in Example 1 was replaced by ethyl 3,4-epoxy-3-methylvalerate, referred to hereinafter as EEMV.

Tests were carried out as described in Example 1 wherein 1,1,1-trichloroethane was stabilised with EEMV (0.5%) together with nitromethane (0.5%) and dioxan (3.5%). The times taken before acidity developed (pH3) in liquid and vapour phases were 120 minutes in both cases.

We claim:

1. A solvent composition comprising 1,1,1-trichloroethane and a stabilising amount ranging from 0.05% to 5% by weight based on the weight of 1,1,1-trichloroethane of a stabilising agent, characterized in that the stabilising agent is an epoxide of the formula.

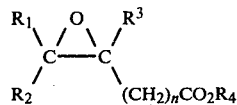

wherein $R_1$, $R_2$ and $R_3$, which may be the same or different, represent a hydrogen atom or an alkyl group having 1 to 4 carbon atoms, and wherein $R_1$ or $R_2$ may also be a phenyl group or a benzyl group, n is 0 or 1, and $R_4$ is an alkyl group having 1 to 2 carbon atoms.

2. A solvent composition as claimed in claim 1 wherein in the stabilising agent the alkyl group represented by and any of $R_1$, $R_2$ and $R_3$ contains 1 or 2 carbon atoms.

3. A solvent composition as claimed in claim 1 or claim 2 wherein in the stabilising agent, $R_1$ and $R_4$ are alkyl groups and $R_2$ and $R_3$ are hydrogen atoms.

4. A solvent composition as claimed in claim 1 or claim 2 wherein in the stabilising agent, $R_1$, $R_3$ and $R_4$ are alkyl groups and $R_2$ is a hydrogen atom.

5. A solvent composition as claimed in claim 1 or claim 2 wherein in the stabilising agent, $R_1$ and $R_4$ are alkyl groups, $R_3$ is a hydrogen atom and $R_2$ is a phenyl group.

6. A solvent composition as claimed in claim 3 wherein the stabilising agent is ethyl trans-2,3-epoxybutyrate.

7. A solvent composition as claimed in claim 4 wherein the stabilising agent is ethyl 3,4-epoxy-3-methylvalerate.

8. A solvent composition as claimed in claim 5 wherein the stabilising agent is ethyl beta-methyl-beta-phenylglycidate.

9. A solvent composition as claimed in any one of the preceding claims which contains one or more additional stabilising agents for 1,1,1-trichloroethane.

10. A solvent composition as claimed in claim 9 wherein the amount of the or each additional stabilising agent is not greater than 3% by weight based on the weight of the 1,1,1-trichloroethane.

11. A method of inhibiting decomposition of 1,1,1-trichloroethane in the presence of metals, which comprises incorporating in the 1,1,1-trichloroethane a stabilising amount of an organic epoxide as defined in any one of claims 1 to 8.

12. A method of degreasing articles which comprises bringing the articles into contact with a solvent composition as claimed in any one of claims 1 to 10, or the vapour thereof.

* * * * *